United States Patent [19]

Parker

[11] 4,000,164
[45] Dec. 28, 1976

[54] HYPOLIPIDEMIC AGENTS

[75] Inventor: Roger Alan Parker, Cincinnati, Ohio

[73] Assignee: Richardson-Merrell Inc., Wilton, Conn.

[22] Filed: Apr. 2, 1973

[21] Appl. No.: 347,232

[52] U.S. Cl. .............................. 260/347.4; 424/285; 260/247.2 B; 260/268 H; 260/293.67; 260/295 R; 260/295.5 R; 260/309; 260/326.36; 260/347.3; 260/347.5

[51] Int. Cl.$^2$ .................................. C07D 307/54

[58] Field of Search ......... 260/347.2, 347.3, 347.5, 260/247.2, 247.3, 347.4

[56] References Cited

UNITED STATES PATENTS 2,834,789    5/1958    Clauson-Kaas .............. 260/347.5

OTHER PUBLICATIONS

M. Stiles "J. of Am. Chem. Soc." vol. 81, 1959 pp. 2598-2599.
Fieser et al. "Reagents for Organic Synthesis" vol. 1 pp. 631-633.
Burger, *Medicinal Chemistry*, part II, 3rd Ed., pp. 1123-1163 (1970).
Dunlop et al., *The Furans*, frontispage and pp. 601 to 608, (NY) Reinhold Pub. Corp. (1953).
*Chemical Abstracts*, vol. 82, abstracts No. 16694h and 16695j (1975).

*Primary Examiner*—John D. Randolph
*Attorney, Agent, or Firm*—L. Ruth Hattan; Eugene O. Retter; George W. Rauchfuss, Jr.

[57] ABSTRACT

Substituted furoylacetic acids and esters, and pharmaceutically acceptable salts thereof of the following general structure are useful as hypolipidemic agents:

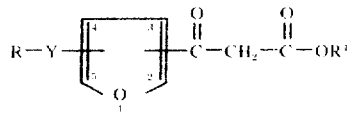

wherein Y represents oxygen or divalent sulfur; R represents a straight or branched alkyl chain containing from 10 to 20 carbon atoms and may be saturated or may be unsaturated containing from 1 to 4 double bonds; R$^1$ represents hydrogen, or an ester group.

4 Claims, No Drawings

HYPOLIPIDEMIC AGENTS

FIELD OF INVENTION

This invention relates to substituted furoylacetic acids and esters and pharmaceutically acceptable salts thereof and their use as hypolipidemic agents.

SUMMARY OF INVENTION

Compounds of the following general Formula I are useful as hypolipidemic agents:

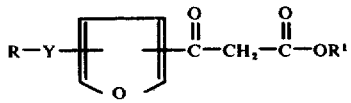

Formula I wherein Y represents oxygen or divalent sulfur; R represents a straight or branched alkyl chain containing from 10 to 20 carbon atoms which may be saturated or may be unsaturated containing from 1 to 4 double bonds; $R^1$ represents hydrogen, straight or branched lower alkyl of from 1 to 6 carbon atoms, benzyl, phenethyl, pyridylmethyl, or Z; Z represents A. the group

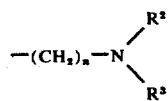

wherein $n$ is an integer of 2 or 3; $R^2$ represents straight or branched lower alkyl of from 1 to 4 carbon atoms or acyl; $R^3$ represents hydrogen or, straight or branched lower alkyl of from 1 to 4 carbon atoms with the proviso that when $R^3$ is hydrogen, $R^2$ is acyl; or when $R^2$ is other than acyl, $R^2$ and $R^3$ taken together with the nitrogen atom to which each is attached form a monocyclic heterocyclic group such as pyrrolidino, piperidino, morpholino, or piperazino; or B. the group

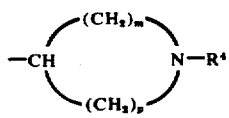

wherein the sum of the integers as represented by $m$ and $p$ is equal to from 3 to 5; and $R^4$ represents straight or branched lower alkyl of from 1 to 4 carbon atoms.

Pharmaceutically acceptable salts of compounds of Formula I wherein $R^1$ represents hydrogen or a basic group are also included within the scope of this invention.

DETAILED DESCRIPTION OF INVENTION

In the above general Formula I the substituent group represented as R—Y— may be attached at any of the positions 2-, 3-, 4-, or 5- of the furan ring. Illustrative examples of straight or branched saturated alkyl groups which R may represent are, for example, decyl, undecyl, dodecyl, tridecyl, tetradecyl, 3,7-dimethyloctyl, 2,4-diethylnonyl, 1-methylundecyl, pentadecyl, hexadecyl, heptadecyl, 3-methyloctadecyl, nonadecyl, didecyl, and the like.

Illustrative examples of straight or branched unsaturated alkyl groups containing from 1 to 3 double bonds which R may represent are, for example, 10-undecenyl, 9,12-octadecadienyl, 3,7,11-trimethyl-2,6,10-hexadecyltrienyl, 3,7-dimethyl-2,6-octadienyl, 5,9-dimethyl-2,4,8-decatrienyl, 4,6-dimethyloct-3-enyl, 1,2,5,9-tetramethyl-2,4,8-decatrienyl, and 11-didecenyl. Both cis- and trans- isomers of the unsaturated alkyl groups are included within the scope of this invention.

Illustrative examples of straight or branched lower alkyl groups which $R^1$ may represent in general Formula I are, for example, methyl, ethyl, n-propyl, isopropyl, n-butyl, tert-butyl, pentyl, and hexyl.

Illustrative examples of straight or branched lower alkyl groups which $R^2$, $R^3$ and $R^4$ may represent in the above general Formula I are, for example, methyl, ethyl, n-propyl, isoproyl, n-butyl and tert-butyl.

The term acyl as represented by $R^2$ in the above general Formula I is taken to mean an alkylcarbonyl radical wherein the alkyl moiety contains from 1 to 4 carbon atoms, such as methyl, ethyl, propyl and butyl.

Pharmaceutically acceptable salts of the compounds of general Formula I wherein $R^1$ represents hydrogen are those formed with any suitable inorganic or organic bases such as those of alkali metals, for example, sodium and potassium; alkaline earth metals, for example, calcium and magnesium, light metals of group III A, for example, aluminum; organic amines such as primary, secondary, or tertiary amines, for example, cyclohexylamine, ethylamine and pyridine. The salts can be prepared by conventional means such as by contacting and neutralizing a solution of a compound of Formula I having a carboxylic acid group in a polar solvent with the stoichiometric quantity of a base, for example, sodium hydroxide. Metal salts also include complex salts, that is metal chelates which may be obtained by the treatment of a furoylacetate of Formula I with a metal acetate, such as cupric acetate or zinc acetate, or by the addition of metal salts, such as calcium or magnesium salts, to a furoylacetic acid of Formula I.

Pharmacetically acceptable salts of the compounds of general Formula I wherein $R^1$ represents a basic group are those of any suitable inorganic or organic acids. Suitable inorganic acids are, for example, hydrochloric, hydrobromic, sulfuric or phosphoric acids and the like. Suitable organic acids are, for example, carboxylic acids such as acetic, propionic, glycolic, lactic, pyruvic, malonic, succinic, fumaric, malic, tartaric, citric, ascorbic, maleic, hydroxymaleic, benzoic, hydroxybenzoic, phenylacetic, cinnamic, salicylic, 2-phenoxybenzoic and the like, or sulfonic acids such as methane sulfonic, 2-hydroxyethane sulfonic acid and the like.

The compounds of this invention can exist in both the keto form as represented by general Formula I and in the enol form as represented by the following general Formula II wherein R, Y and $R^1$ have the meanings defined hereinbefore.

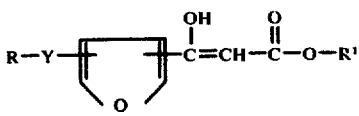

Formula II

For purposes of uniformity the illustrative compounds and specific examples of compounds of this invention are named as the keto form, that is, as represented by general Formula I.

Preferred compounds of this invention are those of general Formulas I and II wherein Y and R are as defined hereinbefore and $R^1$ represents hydrogen straight or branched lower alkyl of from 1 to 4 carbon atoms, such as, methyl, ethyl, isoproyl, butyl, and the like and benzyl.

Illustrative examples of compounds of this invention are, for example, 2-(5-decyloxy-2-furoyl)acetic acid, 2-(5-tetradecyloxy-2-furoyl)acetic acid methyl ester, 2-[5-(cis-9-octadecenyloxy)-2-furoyl]acetic acid ethyl ester, 2-[5-dodecyloxy-2-furoyl]acetic acid benzyl ester, 2-(5-tetradecyloxy-2-furoyl)acetic acid methyl ester, 2-(5-tetradecyloxy-2-furoyl)acetic acid ethyl ester, 2-(5-octadecyloxy-2-furoyl)acetic acid propyl ester, 2-(5-tetradecylthio-2-furoyl)acetic acid, 2-(4-dodecylthio-2-furoyl)acetic acid butyl ester, 2-(3-tridecyloxy-2-furoyl)acetic acid benzyl ester, 2-(5-hexadecyloxy-2-furoyl)acetic acid methyl ester, 2-(5-heptadecyloxy-3-furoyl)acetic acid butyl ester, 2-(4-undecylthio-3-furoyl)acetic acid ethyl ester, 2-(5-hexadecyloxy-2-furoyl)acetic acid diethylaminoethyl ester, 2-(5-pentadecylthio-2-furoyl)acetic acid 3-pyridylmethyl ester, 2-(5-hexadecylthio-2-furoyl)acetic acid methyl ester, 2-(4-decyloxy-2-furoyl)acetic acid, 2-(5-undecyloxy-2-furoyl)acetic acid ethyl ster, 2-(5-nonadecyloxy-2-furoyl)acetic acid phenethyl ester, 2-(5-didecyloxy-2-furoyl)acetic acid propyl ester, 2-(4-didecyloxy-2-furoyl)acetic acid 4-pyridylmethyl ester, 2-(4-dodceylthio-2-furoyl)acetic acid dipropylaminopropyl ester, 2-(5-tetradecyloxy-2-furoyl)acetic acid piperidinoethyl ester, 2-(4-hexadecyloxy-3-furoyl)acetic acid morpholinoethyl ester, 2-(5-undecyloxy-3-furoyl)acetic acid 4-(N-methyl)piperidyl ester, 2-[5-(cis-cis-9,12-octadienyloxy)-3-furoyl]acetic acid methyl ester, 2-[5-(3,7-dimethyloct-6-enyloxy)-2-furoyl]acetic acid ethyl ester.

The compounds of this invention are useful as hypolipidemic agents in that they reduce blood lipids, particularly cholesterol and triglycerides without concurrent accumulation of desmosterol. These compounds can be administered to animals, mammals and humans and are useful in the treatment of hyperlipidemic states such as are encountered in patients with cardiovascular diseases that can result in heart failure and stroke.

The compounds of this invention can be administered orally or parenterally either alone or in the form of pharmaceutical pr parations. Pharmaceutical preparations containing conventional pharmaceutical carriers and as active ingredients compounds of this invention can be employed in unit dosage forms such as solids, for example, tablets, capsules and pills, or liquid solutions, suspensions, or emulsions for oral and parenteral administration. The quantity of compound administered can vary over a wide range to provide from about 0.5 mg/kg (milligrams per kilogram) to about 100 mg/kg of body weight of the patient per day, and preferably from about 10 mg/kg to 30 mg/kg of body weight of the patient per day, to achieve the desired effect. Unit doses can contain from about 50 mg to 1 g of a compound of this invention and may be administered, for example, from 1 to 4 times daily.

The compounds of general formula I wherein $R^1$ is hydrogen may be prepared by reacting an appropriately R-Y- substituted furyl methyl ketone with magnesium methyl carbonate in dimethyl acetamide or dimethyl formamide followed by treatment of the resulting complex with water and a mineral acid, such as, hydrochloric acid. The reaction to obtain the complex may be carried out at temperatures of from −30° C and preferably from −20° C. The reaction time varies from about ½ hour to about 3 days depending upon the reactants and temperature of the reaction.

The R—Y— substituted furyl methyl ketones employed in the above described reaction may be prepared by the reaction of methyl magnesium bromide and the imidazolide derivative of an appropriately R—Y— substituted furoic acid, or by acylating an appropriately R—Y— sustituted furan with an acyl halide, such as acetyl chloride or acetic anhydride under conditions of a Friedel-Crafts acylation reaction. The imidazolide derivative is obtained by treating an appropriately R—Y— substituted furoic acid with N,N'-carbonyldiimidazole or by treatment of the R—Y— substituted furoic acid chloride, obtained by treating the substituted furoic acid with thionyl chloride, with two equivalents of imidazole [H. A. Staab, Angew. Chem. Internat. Edit. vol. 1, 351(1962)]. The R—Y— substituted furan is obtained by thermo (>150° C) decarboxylation of an appropriately R—Y— substituted furoic acid, [D. G. Manly and E. D. Amstutz, J. Org. Chem. 21, 519(1956)]. The appropriately R—Y— substituted furoic acids are prepared by the reaction of an alcohol or a thioalcohol of the formula RYH wherein R and Y have the meanings defined in general Formula I with bromofuroic acid under basic conditions followed by acidification.

The R—Y— substituted furoylacetic acids obtained as described hereinabove may be converted to the esters of this invention, that is, compounds of general Formula I wherein $R^1$ is other than hydrogen, by treating the acid derivative with trifluoroacetic anhydride, N,N'-dicyclohexylcarbodiimide, N,N'-carbonyldiimidazole, or a thionyl halide, such as thionyl chloride, followed by alcoholysis with a compound of the formula $R^1OH$ wherein $R^1$ has the meaning defined in general Formula I except that it is not hydrogen.

The R—Y— substituted furoylacetic acids may also be reacted with diazomethane to give the corresponding methyl ester, which may be converted to esters of higher boiling alcohols of this invention by a standard tranesterification reaction with an alcohol of the formula $R^1OH$ wherein $R^1$ has the meaning defined in general Formula I except that it is not hydrogen or methyl.

The compounds of general Formula I wherein $R^1$ is other than hydrogen may also be prepared by condensing a compound of the formula

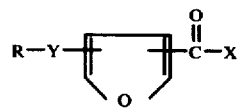

Formula III wherein R and Y have the meanings defined hereinbefore and X represents halogen, 1-imidazole or $OR^5$ wherein $R^5$ represents lower alkyl with either an ester of acetoacetic acid followed by alkaline hydrolysis of the resulting furoylacetoacetate or an ester of acetic acid employing a basic catalyst. These compounds may also be obtained by the acylation of a compound of Formula III wherein X represents halogen or 1-imidazole with a magnesium complex of malonic acid monoester of the following general formula IV, by the general method of R. E. Ireland and J. A. Marshall, J. Am. Chem. Soc. 81, 2907 (1959).

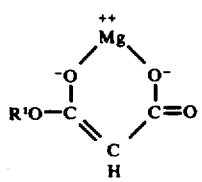

Formula IV

In the above general Formula IV R¹ has the meaning defined in Formula I except that it is not hydrogen. This reaction is carried out in a solvent such as tetrahydrofuran, dimethyl formamide or dimethyl acetamide followed by acid hydrolysis with a mineral acid such as, hydrochloric acid, or with ammonium chloride.

The following specific examples are illustrative of this invention.

EXAMPLE 1

2-[5-(Tetradecyloxy)-2-furoyl]acetic acid

A mixture of 125.0 g (0.652 mole) of 5-bromo-2-furoic acid, 210.0 g (0.978 mole) of 1-tetradecanol 183.0 g (1.630 mole) of potassium tert- butoxide and 2500 ml of dimethyl acetamide is heated with stirring. The tertbutanol formed in the reaction is allowed to distill off, then the mixture is heated to reflux with stirring for 48 hours. To the cooled mixture is added 6 liters of icewater, and the mixture is acidified with malonic acid. The resulting precipitate is collected, dried and recrystallized twice from methanol to give 82.0 g (29%) of 5-(tetradecyloxy)-2-furoic acid, M.P. 112°–115° C (dec.) The 82.0 g (0.253 mole) of 5-(tetradecyloxy)-2-furoic acid, 41.0 g (0.253 mole) of N,N'-carbonyldiimidazole and tetrahydrofuran are combined and stirred at room temperature, during which time carbon dioxide gas is evolved, then cooled to give N-[5-(tetradecyloxy)-2-furoyl]imidazole. The N-substituted imidazole, 50.0 g (0.134 mole) in tetrahydrofuran, is cooled in an ice bath. An equivalent amount of methyl magnesium bromide (50 ml of a 3 Molar solution in ether) is slowly added over 2 hours to the stirred mixture. The reactin is stirred for an additional 3 hours then excess (500 ml.) of 2N HCl is added and the product extracted into ether. The ether layer is separated, washed with water, dried over sodium sulfate, filtered, and evaporated to dryness affording 5-(tetradecyloxy)-2-furyl methyl ketone.

A mixture of magnesium methyl carbonate in dimethyl formamide (300 g of a 2.0 mM/g solution) is heated in a 120° C oil bath with stirring under carbon dioxide flushing for ½ hour. To this mixture is added 32.3 g (0.100 mole) of 5-(tetradecyloxy)-2-furyl methyl ketone, and the oil bath temperature is raised to 130° C to 150° C. Dry nitrogen is flushed through the mixture for 5 hours. The mixture is allowed to cool to room temperature under carbon dioxide flushing after which it is poured slowly into 2 liters of concentrated HCl-ice (1:1) with vigorous stirring. When the evolution of gas is complete the precipitate is collected and washed with cold water, then dried to give 2-[5-(tetradecyloxy)-2-furoyl]acetic acid.

EXAMPLE 2

2-[5-(Tetradecyloxy)-2-furoyl]acetic acid methyl ester

To a cooled suspension of 10.0 g (0.027 mole) of 2-[5-tetradecyloxy)-2-furoyl]acetic acid in 500 ml of anhydrous ether is added 0.1 mole of diazomethane prepared by the method of F. Arndt, Org. Syn. Coll. Vol. 2, 165 (1943), in 200 ml of ether followed by 1.0 ml of borontrifluoride-etherate. The mixture is allowed to stand overnight at room temperature, after which it is poured into iced-water. The ether layer is separated, washed with water, dried over sodium sulfate, filtered, and evaporated to dryness to give 2-[5-(tetradecyloxy)-2-furoyl]acetic acid methyl ester.

EXAMPLE 3

2-[5-(cis-9-Octadecen-1-yloxy)-3-furoyl]acetic acid methyl ester

A mixture of 57.2 g (0.300 mole) of 5-bromo-3-furoic acid, 121.0 g (0.45 mole) of cis-9-octadecenol, 18.0 g (0.750 mole) of sodium hydride and 2 liters of p-xylene are heated to reflux with stirring for 48 hours. The mixture is allowed to cool, then is acidified with acetic acid, and diluted with 2 liters of water. The organic layer is separated, dried, evaporated to dryness, and the residue is recrystallized from hexane to give 5-(cis-9-octadecen-1-yloxy)-3-furoic acid.

To a cooled mixture of 40.0 g (0.106 mole) of 5-(cis-9-octadecen-1-yloxy)-3-furoic acid in methylene chloride is added 30 ml of thionyl chloride. The mixture is stirred for 5 hours. Then the solvent and excess thionyl chloride is removed under reduced pressure affording the crude 5-(cis-9-octadecen-1-yloxy)-3-furoyl chloride. A mixture of 11.6 g (0.100 moles) of methyl acetoacetate and 2.3 g of sodium in 1 liter of benzene is refluxed for 20 hours, then cooled, and the crude 5-(cis-9-octadecen-1-yloxy)-3-furoyl chloride is added over a two hour period. The mixture is refluxed for 6 hours, cooled by the addition of ice and mixed well. The benzene layer is separated, washed with 5% sodium bicarbonate solution and dried. The benzene is distilled off under reduced pressure yielding 2-[5-(cis-9-octadecen-1-yloxy)-3-furoyl]acetoacetic acid, methyl ester. To a solution of 3.3 g of ammonium chloride in 15 ml of water at 40° C is added 10 g of the above ester maintaining the temperature at 40° C for 15 minutes followed by rapid cooling. The solution is extracted with ether, the extract dried, and evaporated to dryness affording 2-[5-(cis-9-octadecen-1-yloxy)-3-furoyl]acetic acid methyl ester.

EXAMPLE 4

2-[5-(9,12,15-Octadecatrien-1-yloxy)-2-furoyl]acetic acid ethyl ester

A mixture of 57.0 g (0.300 mole) of 5-bromo-2-furoic acid, 119.0 g (0.450 mole) of 9,12,15-octadecatrienol, and 84.0 g (0.750 mole) of potassium tert-butoxide in dry toluene is stirred with heating. The tert-butanol formed in the reaction is allowed to distill off and the mixture is refluxed at 110° C with stirring for 48 hours. The mixture is allowed to cool, then is acidified with acetic acid and diluted with ice-water. The toluene organic layer is separated, washed with water, then extracted three times with 5% sodium bicarbonate solution. The combined aqueous extracts are cooled and acidified with 10% HCl solution to give 5-(9,12,15-octadecatrien-1-yloxy)-2-furoic acid.

To 40.0 g (0.107 mole) of 5-(9,12,15-octadecatrien-1-yloxy)-2-furoic acid in anhydrous tetrahydrofuran is added 17.4 g (0.107 mole) of N,N'-carbonyldiimidazole. The mixture is stirred at room temperature until the evolution of carbon dioxide gas ceases to be evolved after which the mixture is evaporated to dryness, and the residue extracted with anhydrous ether. The ether extract is evaporated to dryness affording N-[5-(9,12,15-octadecatrien-1-yloxy)-2-furoyl]imidazole.

Malonic acid monoethyl ester, 14.5 g (0.110 mole) magnesium methoxide, 19.0 g (0.220 mole) and anhydrous tetrahydrofuran are combined and heated with stirring under nitrogen allowing the methanol produced to distill off. N-[5-(9,12,15-octadecatrien-1-yloxy)-2-furoyl]imidazole, 45.0 g (0.105 mole) is added to the above magnesium complex with stirring and cooling on an ice-bath for 4 hours. The solvent is removed and the residue diluted with ice- concentrated HCl (1:1) solution and the desired 2-[5-(9,12,15-octadecatrien-1-yloxy)-2-furoyl]acetic acid ethyl ester is obtained.

EXAMPLE 5

2-[5-(Tetradecyloxy)-2-furoyl]acetic acid benzyl ester

A mixture of 10.0 g (0.027 mole) of 2-[5-(tetradecyloxy)-2-furoyl]acetic acid, 4.4 g (0.027 mole) of N,N'-carbonyldiimidazole, and anhydrous tetrahydrofuran is stirred until the evolution of carbon dioxide stops. The mixture is cooled on an ice bath and 3.0 g (0.027 mole) of benzyl alcohol is added. The reaction is allowed to warm to room temperature and evaporated to dryness. The residue is extracted with ether-$H_2O$. The ether layer is washed with 10%; aqueous HCl, water, saturated sodium chloride, dried with sodium sulfate and evaporated to dryness affording 2-[5-(tetradecyloxy)-2-furoyl]acetic acid benzyl ester.

EXAMPLE 6

2-[5-(Dodecylthio)-2-furoyl]acetic acid

When in Example 1, 1-dodecanethiol is substituted for 1-tetradecanol, 2-[5-(dodecylthio)-2-furoyl]acetic acid is obtained.

EXAMPLE 7

2-[5-(Dodecylthio)-2-furoyl]acetic acid 2-acetamidoethyl ester

A mixture of 20.0 g (0.057 mole) of 2-[5-(dodecylthio)-2-furoyl]acetic acid, 9.2 g (0.057 mole) of N,N'-carbonyldiimidazole and tetrahydrofuran is stirred for 4 hours, after which 5.9 g (0.057 mole) of N-acetylethanolamine is added. The mixture is stirred at room temperature overnight, then is diluted with ice cold 5% aqueous hydrochloric acid and extracted with ether. The ether layer is washed in water and saturated sodium chloride solution, dried with sodium sulfate, and evaporated to dryness to yield 2-[5-(dodecylthio)-2-furoyl]-acetic acid 2-acetamidoethyl ester.

EXAMPLE 8

2-[5-(3,7,11-Trimethyldodecyloxy)-2-furoyl]acetic acid 2-dimethylaminoethyl ester When in Example 1, 3,7,11-trimethyl-1-dodecanol is substituted for 1-tetradecanol, 2-[5-(3,7,11-trimethyldodecyloxy)-2-furoyl]acetic acid is obtained. This acid is combined with equal moles of N,N'-carbonyldiimidazole and 2-dimethylaminoethanol in anhydrous tetrahydrofuran. The solvent is removed under reduced pressure, and the residue is extracted with ether-water. The ether layer is evaporated to dryness affording 2-[5-(3,7,11-trimethyldodecyloxy)-2-furoyl]acetic acid 2-dimethylaminoethyl ester. By dissolving 2-[5-(3,7,11-trimethyldodecyloxy)-2-furoyl]acetic acid 2-dimethylaminoethyl ester in ether followed by treatment of the solution with one equivalent of HCl gas and collecting the precipitate gives 2-[5-(3,7,11-trimethyldodecyloxy)-2-furoyl]acetic acid 2-diethylaminoethyl ester hydrochloride.

EXAMPLE 9

An illustrative composition for tablets is as follows:

|     |                                                    | Per Tablet |
| --- | -------------------------------------------------- | ---------- |
| (a) | 2-[5-(tetradecyloxy)-2-furoyl]-acetic acid methyl ester | 100.0 mg |
| (b) | wheat starch                                       | 15.0 mg    |
| (c) | lactose                                            | 33.5 mg    |
| (d) | magnesium stearate                                 | 1.5 mg     |

A portion of the wheat starch is used to make a granulated starch paste which together with the remainder of the wheat starch and the lactose is granulated, screened and mixed with the active ingredient (a), and the magnesium stearate. The mixture is compressed into tablets weighing 150 mg each.

EXAMPLE 10

An illustrative composition for a parenteral injection is the following wherein the quantities are on a weight to volume bases.

|     |                                                    | Amount   |
| --- | -------------------------------------------------- | -------- |
| (a) | 2-[5-(3,7,11-trimethyldodecyloxy)-2-furoyl]acetic acid 2-diethylaminoethyl ester hydrochloride | 100.0 mg |
| (b) | sodium chloride                                    | q.s.     |
| (c) | water for injection to make                        | 20.0 ml  |

The composition is prepared by dissolving the active ingredient (a) and sufficient sodium chloride in water for injection to render the solution isotonic. The composition may be dispensed in a single ampule containing 100 mg of the active ingredient for multiple dosage or in 20 ampules for single dosage.

EXAMPLE 11

An illustrative composition for hard gelatin capsules is as follows:

|     |                                                    | Amount   |
| --- | -------------------------------------------------- | -------- |
| (a) | 2-[5-(tetradecyloxy)-2-furoyl]-acetic acid methyl ester | 200.0 mg |
| (b) | talc                                               | 35.0 mg  |

The composition is prepared by passing the dry powders of (a) and (b) through a fine mesh screen and mixing them well. The powder is then filled into No. 0 hard gelatin capsules at a net fill of 235 mg per capsule.

I claim:

1. A compound selected from the formula:

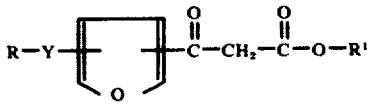

wherein Y is selected from oxygen or divalent sulfur; R is selected from a straight or branched saturated alkyl group of from 10 to 20 carbon atoms or a straight or branched unsaturated alkyl group of from 10 to 20 carbon atoms having from 1 to 4 double bonds; $R^1$ is selected from hydrogen, a straight or branched lower alkyl group of from 1 to 6 carbon atoms, benzyl or phenethyl and pharmaceutically acceptable salts thereof.

2. A compound of claim 1 wherein $R^1$ is selected from hydrogen or a straight or branched lower alkyl group of from 1 to 4 carbon atoms.

3. A compound of claim 2 wherein R contains from 12 to 17 carbon atoms.

4. A compound of claim 1 wherein the R-Y substituent is attached to the 5- position of the furan ring, and the

substituent is attached to the 2- position of the furan ring.

* * * * *

UNITED STATES PATENT AND TRADEMARK OFFICE
CERTIFICATE OF CORRECTION

PATENT NO. : 4,000,164
DATED : December 28, 1976
INVENTOR(S) : Roger Alan Parker It is certified that error appears in the above—identified patent and that said Letters Patent are hereby corrected as shown below:

Column 3, line 5, "isoproyl" should read "isopropyl"; line 25, "ethyl ster" should read "ethyl ester". Column 4, lines 2 and 3, "temperatures of from -30°C and preferably from -20°C." should read "temperatures of from -30° to 50°C and preferably from -20° to about 25°C."; line 11, "sustituted" should read "substituted".

*Signed and Sealed this*

*Twenty-ninth* Day of *November 1977*

[SEAL]

Attest:

RUTH C. MASON
*Attesting Officer*

LUTRELLE F. PARKER
*Acting Commissioner of Patents and Trademarks*